(12) United States Patent
Olah et al.

(10) Patent No.: US 7,795,175 B2
(45) Date of Patent: Sep. 14, 2010

(54) NANO-STRUCTURE SUPPORTED SOLID REGENERATIVE POLYAMINE AND POLYAMINE POLYOL ABSORBENTS FOR THE SEPARATION OF CARBON DIOXIDE FROM GAS MIXTURES INCLUDING THE AIR

(75) Inventors: George A. Olah, Beverly Hills, CA (US); Alain Goepert, Alhambra, CA (US); Sergio Meth, Los Angeles, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 459 days.

(21) Appl. No.: 11/780,244

(22) Filed: Jul. 19, 2007

(65) Prior Publication Data

US 2008/0293976 A1    Nov. 27, 2008

Related U.S. Application Data

(60) Provisional application No. 60/837,274, filed on Aug. 10, 2006.

(51) Int. Cl.
  *B01J 20/22* (2006.01)
(52) U.S. Cl. .................... 502/401; 502/400
(58) Field of Classification Search ............... 502/400, 502/401
  See application file for complete search history.

(56) References Cited

U.S. PATENT DOCUMENTS

| 4,243,613 | A | 1/1981 | Brockhaus et al. ......... 568/482 |
| 4,762,528 | A | 8/1988 | Reichl ........................ 44/51 |
| 4,810,266 | A | 3/1989 | Zinnen et al. ................ 55/68 |
| 5,087,597 | A | 2/1992 | Leal et al. .................. 502/62 |
| 5,364,887 | A | 11/1994 | Konig et al. ............... 518/713 |
| 5,376,614 | A | 12/1994 | Birbara et al. ............. 502/402 |
| 5,492,683 | A | 2/1996 | Birbara et al. ............. 423/230 |
| 5,876,488 | A | 3/1999 | Birbara et al. ............. 96/111 |
| 5,928,806 | A | 7/1999 | Olah et al. .................. 429/13 |
| 6,364,938 | B1 | 4/2002 | Birbara et al. ............. 95/139 |
| 6,540,936 | B1 | 4/2003 | Takagi et al. ............. 252/184 |
| 6,547,854 | B1 | 4/2003 | Gray et al. ................ 95/139 |
| 6,908,497 | B1 | 6/2005 | Sirwardane ................ 95/136 |

FOREIGN PATENT DOCUMENTS

| EP | 1 180 511 A1 | 2/2002 |
| EP | 1 234 947 A2 | 8/2002 |
| FR | 2 543 946 A1 | 10/1984 |
| JP | 59-216839 | 12/1984 |
| WO | WO 98/29187 A1 | 7/1998 |
| WO | WO 2005/026694 A2 | 3/2005 |
| WO | WO 2005/037746 A1 | 4/2005 |

OTHER PUBLICATIONS

English abstract, CN 1 303 910 A (Jul. 18, 2001).
English abstract, JP 2006-021989 A (Jan. 26, 2006).
Ochoa-Fernandez et al., "Nanocrystalline Lithium Zirconate with Improved Kinetics for High-Temperature $CO_2$ Capture," Chem. Mater. 18: 1383-1385 (2006).
Xu et al., "Preparation and characterization of novel $CO_2$ 'molecular basket' adsorbents based on polymer-modified mesoporous molecular sieve MCM-41," Microporous and Mesoporous Materials 62: 29-45 (2003).
International Search Report and Written Opinion of the International Searching Authority, dated Dec. 18, 2007, from corresponding International application No. PCT/US2007/074615.
Ashby, E.C. et al., "Concerning the Formation of Hydrogen in Nuclear Waste. Quantitative Generation of Hydrogen Via a Cannizzaro Intermediate," J. Am. Chem. Soc., Vol. 115, pp. 1171-1173 (1993).

*Primary Examiner*—Edward M Johnson
(74) *Attorney, Agent, or Firm*—Winston & Strawn LLP

(57) ABSTRACT

The invention relates to regenerative, supported amine sorbents that includes an amine or an amine/polyol composition deposited on a nano-structured support such as nanosilica. The sorbent provides structural integrity, as well as high selectivity and increased capacity for efficiently capturing carbon dioxide from gas mixtures, including the air. The sorbent is regenerative, and can be used through multiple operations of absorption-desorption cycles.

26 Claims, No Drawings

NANO-STRUCTURE SUPPORTED SOLID REGENERATIVE POLYAMINE AND POLYAMINE POLYOL ABSORBENTS FOR THE SEPARATION OF CARBON DIOXIDE FROM GAS MIXTURES INCLUDING THE AIR

This application claims the benefit of U.S. application 60/837,274 filed Aug. 10, 2006, the entire content of which is expressly incorporated herein by reference thereto.

FIELD OF THE INVENTION

The invention relates to nano-structure supported (such as fumed silica, alumina and the like solid) regenerative polyamine-polyol absorbents for capturing and separating carbon dioxide from gas mixtures, including the air.

BACKGROUND OF THE INVENTION

Climate change and global warming is considered one of the most pressing and severe environmental problems of today. It is now generally accepted that the main cause for global warming is the release of the so-called greenhouse gases into the atmosphere. A major greenhouse gas is carbon dioxide ($CO_2$), which is released predominantly from combustion of fossil fuels such as coal, petroleum and natural gas. Together, these fossil fuels supply about 80% of the energy needs of the world. Because fossil fuels are still relatively inexpensive and easy to use, and since no satisfactory alternatives are yet available to replace them on the enormous scale needed, fossil fuels are expected to remain our main source of energy in the long term.

One way to mitigate $CO_2$ emissions and their influence on the global climate is to efficiently and economically capture $CO_2$ from its source, such as emissions from fossil fuel-burning power plants and other industrial factories, naturally occurring $CO_2$ accompanying natural gas, and the air. Once captured, $CO_2$ can be sequestered in geological formations or under the sea, or can be used as a raw material to synthesize fuel and synthetic hydrocarbons.

Currently, separation and removal of $CO_2$ from gas streams is achieved by techniques based on physical and chemical processes such as absorption by liquid solution systems, adsorption onto solid systems, cryogenic separation, and permeation through membranes.

Among various $CO_2$ separation techniques, amine solution-based $CO_2$ absorption/desorption systems are one of the most suitable for capturing $CO_2$ from high volume gas streams. Commonly used solvents in such systems are aqueous solutions of alkanolamines such as monoethanolamine (MEA), diethanolamine (DEA), diisopropanolamine (DIPA), and methydiethanolamine (MDEA). Certain sterically hindered amines, such as 2-amino-2-methyl-1-propanol (AMP), can also be used as absorbents because of their high $CO_2$ loading capacities. Of these, MEA is most widely used because of its high $CO_2$ absorption rate, which allows use of shorter absorption columns. However, MEA system presents major drawbacks, including the large amount of heat required to regenerate the solvent and operational problems caused by corrosion and chemical degradation. To prevent excessive corrosion, typically only 10 to 30 weight % MEA is used in an aqueous amine solution, with the rest being water. Because the entire solution, of which 70 to 90% is water, must be heated to regenerate the MEA system, a lot of energy is wasted during the regeneration process. Other alkanolamine systems also present disadvantages. For example, secondary and hindered amines (e.g., DEA, DIPA, AMP) provide more moderate $CO_2$ absorption rates than MEA, and are also prone to corrosion and chemical degradation. MDEA is known to absorb $CO_2$ only at a slow rate. Formulations formed by blending several alkanolamines are of interest because they can combine favorable characteristics of various compounds while suppressing in part their unfavorable characteristics. A number of blended alkanolamine solutions have been developed, and the most common blends are MDEA-based solution containing MEA or DEA. However, blended alkanolamine solutions do not eliminate the drawbacks of amine solution-based systems.

$CO_2$ can also be captured by adsorption on solid sorbents. Solids are typically used as a physical adsorbent for separation of $CO_2$. Such processes are based on the ability of porous solids to reversibly adsorb certain components in a mixture. The solids can have a large distribution of pore size, as in silica gel, alumina, and activated carbon, or a pore size controlled by the crystal structure, e.g., zeolites. At low temperatures like room temperature, zeolite-based adsorbents have high $CO_2$ absorption capacities (e.g., 160 mg $CO_2$/g for zeolite 13X and 135 mg $CO_2$/g for zeolite 4A at 25° C. in pure $CO_2$). However, the adsorption capacities of these adsorbents decline rapidly with increasing temperature. Further, because gases are only physically adsorbed on the adsorbents, actual separation of an individual gas from a mixture of gases is low.

To achieve a higher selectivity for $CO_2$ adsorption, a compound providing chemical absorption can be applied on the solid adsorbent. For this purpose, an amine or polyamine can be deposited or grafted onto a solid support. Amines and polyamines chemically bound (grafted) on the surface of solids, such as silicas and alumina-silicas, however, show limited absorption capacity of less than 80 mg $CO_2$/g and, in most cases, less than 50-60 mg $CO_2$/g absorbent. For example, U.S. Pat. No. 5,087,597 to Leal et al. discloses a method for chemisorption of $CO_2$ at room temperature using silica gel having a surface area between 120 and 240 $m^2$/g, which is modified with a polyalkoxysilane containing one or more amino moieties in its structure. The material is disclosed to be capable of absorbing between 15 and 23 mg of dry $CO_2$ per gram of absorbent. U.S. Pat. No. 6,547,854 to Gray et al. discloses a method for preparing amine-enriched sorbents by incorporating the amine onto the surface of oxidized solids. The reported maximum amount of $CO_2$ absorbed on these solids is 7.7 mg/g absorbent using a gas mixture of 10% $CO_2$ in He. As is evident from the data, the amount of $CO_2$ that can be absorbed on the grafted amino group on various solid supports remains relatively low, because of their low amine coverage.

A more promising pathway involves impregnating a solid support with amines or polyamines. For example, a paper by S. Satyapal et al., *J. Energy and Fuels* 15:250 (2001) describe the development of polyethylenimine (PEI)/polyethylene glycol (PEG) on a high surface area polymethylmethacrylate polymeric support. This solid is currently used in space shuttles to remove $CO_2$ from the cabin atmosphere and release it into the space. Its capacity is approximately 40 mg $CO_2$/g absorbent at 50° C. and 0.02 atm. $CO_2$. This material and its modifications are disclosed in U.S. Pat. Nos. 6,364,938; 5,876,488; 5,492,683; and 5,376,614 to Birbara et al. The preferred supports described in these patents are of polymeric nature, with acrylic ester resins such as AMBERLITE® being described as having particularly suitable characteristics. U.S. Pat. Nos. 5,376,614; 5,492,683; and 5,876,488 also disclose other possible supports, including alumina, zeolite and carbon molecular sieves. According to U.S. Pat.

Nos. 5,492,683 and 5,376,614, however, the amount of amine present on the sorbent is limited, ranging from 1 wt. % to 25 wt. %.

U.S. Pat. No. 4,810,266 to Zinnen et al. discloses a method for creating $CO_2$ sorbents by treating carbon molecular sieves with amine alcohols. This patent discloses that monoethanolamine (MEA)-based materials are not stable and release MEA during the regeneration step at higher temperatures. International Publication No. WO 2004/054708 discloses absorbents based on mesoporous silica supports. The active components for $CO_2$ absorption are amines or mixture thereof chemically connected or physically adsorbed on the surface of the mesoporous silicas. Absorption on most of the absorbents described in this publication is below 70 mg $CO_2$/g. The best results are obtained by using diethanolamine (DEA), which is physically adsorbed on the support (about 130 mg $CO_2$/g). However, because of the volatility of DEA under the desorption conditions, the effectiveness of this absorbent generally decrease with increasing number of $CO_2$ absorption-desorption cycle (about 16.8% after 5 cycles at a moderate regeneration temperature of only 60° C.). U.S. Pat. No. 6,908,497 to Sirwardane et al. discloses a method for preparing sorbents by treating a clay substrate having a low surface area of 0.72 to 26 $mg^2$/g with an amine and/or ether.

Alcohols, polyethylene glycol and other oxygenated compounds have also been used for decades for acid gas removal, mainly $CO_2$ and $H_2S$. For example, SELEXOL® from Union Carbide (now Dow Chemicals) and SEPASOLV MPE® from BASF are used in commercial processes. Oxygenated compounds in combination with amines as mixed physical or chemical sorbents, in a process such as a glycol-amine process, have also been used for many years for acid gas removal (see Kohl, A. L. and Nielsen, R. B., GAS PURIFICATION 5th ed. (Gulf Publishing Co.)). U.S. Pat. No. 4,044,100 to McElroy demonstrates the use of mixtures of diisopropanolamine and dialkyl ethers of a polyethylene glycol for removing gases, including $CO_2$ from gaseous streams. The use of ethylene glycol to improve the absorption and desorption of $CO_2$ from amines has also been studied by J. Yeh et al., *Energy and Fuels* 15, pp. 274-78 (2001). While the literature mainly relates to the use of amines and oxygenated compounds in the liquid phase, the use of oxygenated compounds to improve characteristics of gas sorbents in the solid phase has also been explored. S. Satyapal et al., *Energy and Fuels* 15:250 (2001) mentions the use of polyethylene glycol in conjunction with polyethyleneimine on a polymeric support to remove $CO_2$ from the closed atmosphere of a space shuttle. X. Xu et al., *Microporous and Mesoporous Materials* 62:29 (2003) shows that polyethylene glycol incorporated in a mesoporous MCM-41/polyethyleneimine sorbent improves the $CO_2$ absorption and desorption characteristics of the tested material. Preparation and performance of a solid absorbent consisting of PEI deposited on a mesoporous MCM-41 is also disclosed (see X. Xu et al., *Energy and Fuels* 16:1463 (2002)). U.S. Pat. Nos. 5,376,614 and 5,492,683 to Birbara et al. use polyols to improve absorption and desorption qualities of the absorbents.

Another new material for trapping carbon dioxide are metal organic framework compounds. A preferred compound known as MOF-177 (J. Am. Chem. Soc., 2005, 127, 17998) has a room temperature carbon dioxide capacity of 140 weight percent at a relatively high pressure of 30 bar.

As these disclosures show, there is a need for an improved sorbent for capturing $CO_2$, which is efficient, economical, readily available and regenerative, and which provides a high removal capacity at ambient as well as elevated temperatures.

In addition, an efficient absorption system that solves the corrosion and evaporation problems of the existing technologies is needed.

SUMMARY OF THE INVENTION

The invention provides supported amine sorbents comprising an amine or an amine/polyol composition deposited on a nano-structured support, which provide structural integrity and increased $CO_2$ absorption capacity.

The support for the amine and amine/polyol compositions is composed of a nano-structured solid. The nano-structured support can have a primary particle size less than about 100 nm, and can be nanosilica, fumed or precipitated oxide, calcium silicate, carbon nanotube, or a mixture thereof. The amine can be a primary, secondary, or tertiary amine or alkanolamine, aromatic amine, mixed amines or combinations thereof. In an example, the amine is present in an amount of about 25% to 75% by weight of the sorbent. The polyol can be selected from, for example, glycerol, oligomers of ethylene glycol, polyethylene glycol, polyethylene oxides, and ethers, modifications and mixtures thereof, and can be provided in an amount up to about 25% by weight of the sorbent.

According to an embodiment, the sorbent is regenerative. The sorbent can be desorbed and regenerated by applying heat, reduced pressure, vacuum, gas purge, lean sweep gas, or a combination thereof.

The invention also relates to preparation of the sorbent and the particular use of the sorbent for capturing and separating carbon dioxide from a gas source. The carbon dioxide can be released and used to produce methanol. The method comprises reduction of carbon dioxide and water, or reduction of carbon dioxide under conditions sufficient to produce an intermediate compound followed by catalytic hydrogenation of the intermediate compound with hydrogen to form methanol.

In one embodiment, methanol is produced by catalytic hydrogenation of an intermediate compound, e.g., methyl formate, wherein the hydrogen used in the hydrogenation is obtained by electrolysis of water obtained from the air. In another embodiment, methanol is produced by reducing the carbon dioxide under conditions sufficient to carbon monoxide, reacting the carbon monoxide with methanol under conditions sufficient to obtain methyl formate, and catalytically hydrogenating the methyl formate under conditions sufficient to produce methanol.

Methanol produced according to the invention can be further processed to any desired derivative or modified compounds. For example, methanol can be dehydrated to produce dimethyl ether, which can also be further treated under conditions sufficient to form compounds such as ethylene and propylene. Ethylene and propylene can be converted to higher olefins, a synthetic hydrocarbons, aromatics, or related products, and therefore are useful as a feedstock for chemicals or as transportation fuel.

In a further embodiment, methanol can be further used for microbiological production of single cell proteins.

DETAILED DESCRIPTION OF THE PREFERRED EMBODIMENTS

The invention relates to regenerative supported sorbents for absorbing $CO_2$.

The sorbent comprises an amine on a nano-structured support, e.g., a nanosilica support, for absorbing and desorbing $CO_2$. $CO_2$ can be absorbed from any desired source, including industrial exhausts, flue gases of fossil fuel-burning power plants, as well as natural sources. The nano-structured support according to the invention provides structural integrity to the amine as well as a high surface area for solid-gas contact. A polyol can also be added to the supported amine sorbent to enhance its $CO_2$ absorption capabilities and $CO_2$ absorption rates.

It has been unexpectedly discovered that certain carriers of nano-scale particles, particularly silica nanoparticles (nanosilica), have exceptional qualities as support for amines, polyamines, polymeric amines, and modifications thereof, for the absorption of $CO_2$. The sorbent with nano-scale support according to the invention provides significant advantages over the absorbents of the prior art, e.g., absorbents having a polymeric support, including a high $CO_2$-selectivity and removal capacity at ambient and elevated temperatures. Thus, the present sorbent allows selective capture and separation of $CO_2$ from various gas mixtures under various conditions and temperatures. The present sorbent is also easy to regenerate and recycle at ambient to moderate temperatures, enabling multiple absorption-desorption cycles with no or minimal loss of activity. The sorbent also addresses the corrosion and evaporation problems of the prior art absorbents. Further, unlike certain prior art sorbents which can contain amine only in an amount of 1 wt. % to 25 wt. %, the nanoparticle-based amine sorbent according to the invention can contain a significantly higher amount of amine, e.g., between about 25 wt. % and 75 wt. %.

Thus, the present sorbent system is practical for separating $CO_2$ from industrial effluent gases such as those from fossil fuel-burning power plants and other industrial factories, as well as other gas streams, particularly natural gas containing significant $CO_2$ concentrations. Significantly, the sorbent can also be used to separate $CO_2$ from the atmospheric air.

The sorbent according to the invention is suggested to absorb $CO_2$ by the following mechanism. Upon contact with a gaseous stream containing $CO_2$, the supported amine chemically absorbs $CO_2$ by forming a carbamate complex.

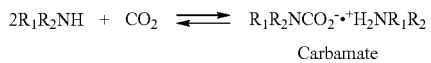

In the presence of water, the carbamate further reacts to form a bicarbonate and releases the amine, which can further react with $CO_2$, thereby increasing the overall $CO_2$ absorption capacity.

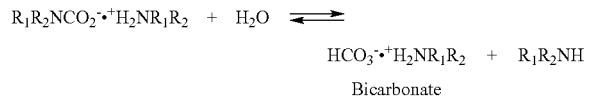

According to an embodiment of the invention, the absorbed $CO_2$ can be readily desorbed and the supported amine can be regenerated. The desorption of $CO_2$ and regeneration of the sorbent can be achieved by modest heating of the sorbent, applying reduced pressure or vacuum, gas purge, and/or a carbon dioxide lean sweep gas, which releases $CO_2$ from the sorbent. The ready regeneration enables the sorbent to undergo repeated absorption-desorption cycles with ease.

Advantageously, a large variety of amine- and ether-based compounds can be used on the present nano-structured support.

Amines that can be used in the invention include primary, secondary and tertiary alkyl- and alkanolamines, aromatic amines, mixed amines, and combinations thereof. Primary and secondary amines are the most active for $CO_2$ absorption. The amine absorbent should, therefore, preferably contain a sufficient amount of primary and secondary amino components. The amino components should also have low volatility to avoid or minimize loss of amine, which would contaminate the gas stream and decrease the effectiveness of the absorption system over time. Examples of amino components include but are not limited to monoethanolamine (MEA), diethanolamine (DEA), methyldiethanolamine, 2-(2-aminoethylamino)-ethanol, diisopropanolamine, 2-amino-2-methyl-1,3-propanediol, triethanolamine, tetraethylenepentamine, pentaethylene-hexamine, polyethyleneimine, and the likes, including various polymeric amine compounds and mixtures thereof. Polyethyleneimines are preferred because of their high proportion of secondary and primary amino functionalities and their low volatility. Polyethyleneimines also provide a high nitrogen/carbon ratio beneficial for maximizing the amount of amino functionalities in the absorbent. Polyethyleneimines having molecular weight greater than 600 are especially preferred. The amine content in the sorbent can be about 25% to about 75% of the total weight of the sorbent.

To enhance the $CO_2$ absorption and desorption characteristics of the supported amine sorbent, polyols can be incorporated in the sorbent composition, in an amount up to 25% of the total weight of the sorbent. The additions of polyols improves the absorption and desorption of the sorbent, and decreases the viscosity of the amines, allowing $CO_2$ to have better access to the active amino sites of the sorbent even at lower temperatures (<50° C.). Polyols used in the invention should be unreactive toward amines, and should have low volatility to avoid or minimize gas loss, which contaminates the gas stream and decreases the effectiveness of the absorption system over time. Examples of polyols used in the present sorbent include but are not limited to glycerol, oligomers of ethylene glycol, polyethylene glycols, polyethylene oxides, ethers of oligomers of ethylene glycol, ethers of polyethylene glycols, ethers of polyethylene oxides, oligomers or polymers of cyclic ethers such as polytetrahydrofuran, and modifications and mixtures thereof. Preferred polyols have a molecular weight lower than 10,000. More preferably, polyols have a molecular weight lower than 1,000.

The support according to the invention is a material having primary particle sizes less than 1,000 nm, preferably less than about 100 nm. Preferred supports are nanosilica, especially so-called fumed silica and precipitated silica. Fumed silica typically has a primary particle size ranging from 5 to 50 nm and a specific surface area between 50 and 500 m$^2$/g. Fumed silica is generally prepared by vapor phase hydrolysis of a silicon-bearing halide, such as silicon tetrachloride (SiCl$_4$). Examples of commercially available fumed silica include AEROSIL® from Degussa, CAB-O-SIL® from Cabot, and REOLOSIL® from Tokuyama. Precipitated silica is formed from aqueous solutions by reaction of an alkaline silicate (e.g., sodium silicate) with a mineral acid (e.g., sulfuric acid) under stirring. Primary particles formed by this method are generally between 3 and 50 nm in size. These primary particles can subsequently aggregate to form larger micron size particles. The specific surface area of precipitated silica generally ranges from 50 to 500 m$^2$/g. Examples of commercially available precipitated silica include HI-SIL® from PPG Industries and FINESIL® and TOKUSIL® from Tokuyama.

Fumed silica and precipitated silica have the appearance of a lightweight, fluffy, white powder. Their small particle size allows them to absorb and retain significant amounts of amines while maintaining free flowing powder characteristics without caking. Another advantage of fumed and precipitated silicas is their non-toxicity. The non-toxicity allows them to be used in food processing, e.g., as anti-caking additives in powdered food products such as milk substitutes, and in cosmetic products, e.g., in abrasive material in a toothpaste. Fumed and precipitated silicas are generally hydrophilic, but their surface can be treated to produce hydrophobic silicas. Both hydrophilic and hydrophobic silicas, as well as other modified silicas, are all suitable for use as the nano-structured amine support according to the invention.

Other nano-structured materials suitable for use in the present amine sorbents include fumed or precipitated oxides such as fumed aluminum oxide, fumed zirconium oxide, and fumed titanium oxide, precipitated aluminum oxide, precipitated titanium oxide, precipitated zirconium oxide, calcium silicate, carbon nanotubes, and mixtures thereof.

The supported amine sorbent can be prepared by impregnation or by another conventional technique. For example, when impregnation is used, the nano-structured support material is mixed or dispersed in a suitable solvent and maintained as a suspension by stirring. A separate amine solution is prepared by completely dissolving the amine in the solvent. The nano-structured support and the amine solution are then combined under stirring. Preferably, the amine solution is added stepwise to the suspension of the support to ensure good dispersion of the amine on the surface of the support. The solvent is then removed to form the supported amine sorbent. The resulting amine sorbent can be used as is or can be crushed and sieved to obtain a uniform powder.

Polyols can be added to enhance the absorption/desorption characteristics of the supported amine sorbent. When a polyol is used, the polyol can be mixed together with the amine solution and added to the suspension of the support. The polyol can also be separately dissolved in the solvent and combined with the suspension of the support. In that case, the polyol solution is preferably added first to the suspension of the support, and the solvent is then removed to obtain the supported polyol material. The obtained solid is then dispersed in the solvent and a solution of the amine in the solvent is added under stirring. Finally, solvent is removed to form the supported amine/polyol sorbent. The sorbent can be used as is or can be crushed and sieved to obtain a uniform powder.

Any solvent which is capable of dissolving, but which does not react with, the amine and the polyol can be utilized. The solvent should preferably be easily separated from the sorbent by mild heating and/or vacuum. Preferred solvents include but are not limited to alcohols, which can dissolve amines and polyols and can be easily removed from the sorbent. For example, methanol, ethanol, and isopropyl alcohol, and various mixtures thereof can be used.

The methods for preparing amine supported sorbents according to the invention are inexpensive and easy to carry out, yet produce sorbents that are superior to the sorbents prepared by previously known methods.

Advantageously, the invention enables a wide range of $CO_2$ absorbing capabilities for use with various natural and industrial gas sources. The absorption can be performed under various conditions, e.g., over a temperature range of 0 to 100° C., and in any suitable manner, e.g., in a regular flow system or in a fixed, moving, or fluidized absorption bed. The ability of the sorbent to capture $CO_2$ can be demonstrated by measuring absorption by thermogravimetry (TGA) or by measuring $CO_2$ absorption under static conditions.

Once the bulk of the amines, e.g., about 70 to 90%, is complexed with $CO_2$, the sorbent can be regenerated. As used herein, the term "regeneration" or "regenerative" is understood to mean that the sorbent can be re-used by releasing or desorbing the absorbed gas from the sorbent. The absorbed gas is released by treating the sorbent with any process that effects the release, e.g., heating, reduced pressure, vacuum, gas purge, and combinations thereof. Thus, the regenerated sorbent according to the invention can be used repeatedly, through multiple absorption-desorption cycles. In an example, the sorbent maintains its absorption efficiency even after repeated absorption-desorption cycles. Preferably, the sorbent maintains its absorption efficiency for many absorption-desorption cycles. It is convenient to use parallel absorption beds, which allow absorption and desorption/regeneration to be carried out continuously.

For example, for a $CO_2$ sorbent, the regeneration is endothermic, so the absorbed $CO_2$ is released by subjecting the absorbent to elevated temperature (e.g., by heating the sorbent at temperatures from about 25° C. to about 120° C.), reduced pressure (e.g., by pressure swing absorption (PSA)), gas purge, vacuum, lean gas sweep, or any combinations thereof. The regeneration treatment allows essentially most of the $CO_2$ that is complexed with the amine of the sorbent to be released. The $CO_2$ can then be stored or used in any desired manner, and the sorbent freed (regenerated) from $CO_2$ is reused in further $CO_2$ absorption-desorption cycles.

Uses and reactions of $CO_2$ include those mentioned above and as further disclosed in co-pending U.S. Patent Application No. 60/837,273 filed Aug. 10, 2006, the entire content of which is incorporated herein by reference thereto.

The sorbent according to the invention is thermally stable and does not release the supported amine in the temperature and/or pressure range of the absorption operation. Further, because it is capable of regeneration and effective operation at a temperature range that can be easily maintained throughout the process, the sorbent is cost-effective for providing a high efficacy and a long life span, in addition to a high selectivity and capacity for $CO_2$ capture and separation. Because of its flexibility and versatility, the sorbent can also advantageously be used to treat large volumes of $CO_2$-containing gases from various sources.

EXAMPLES

The following examples are illustrative only and should not be interpreted as limiting the scope of the invention.

Example I

Preparation of a Supported Amine Sorbent

This example illustrates preparation of a supported amine sorbent composed of 50 wt. % polyethylenimine and 50 wt. % fumed silica having an average primary particle size of 7 nm and a specific surface area of 390 $m^2/g+/-40\ m^2/g$.

Polyethylenimine (molecular weight $M_w$ of 25,000) 4 g was dissolved in 25 mL of methanol. This solution was then added drop-wise under stirring to 4 g fumed silica in suspension in 100 mL methanol to ensure good dispersion of polyethylenimine on the support. The mixture was stirred for an additional hour, and the solvent was then removed from the mixture by heating at 50° C. under vacuum on a rotovap followed by overnight vacuum (<1 mm Hg). The supported amine sorbent obtained was a white solid, which was then crushed and sieved to produce a uniform powder.

Example II

Preparation of a Supported Amine/Polyol Sorbent

This example illustrates preparation of a supported amine/polyol sorbent composed of 45 wt. % polyethylenimine, 10 wt. % polyethylene glycol, and 45 wt. % fumed silica of having an average primary particle size of 7 nm with a specific surface area of 390 m²/g+/−40 m²/g.

Polyethylene glycol (molecular weight $M_w$ of 400) 2 g was dissolved in 25 mL of methanol. This solution was then added drop-wise to 9 g fumed silica suspended in 200 mL methanol, under stirring, to ensure good dispersion of polyethylene glycol on the support. The mixture was then stirred for an additional hour. Thereafter, the solvent was removed from the mixture by heating at 50° C. under vacuum on a rotovap, followed by overnight vacuum (<1 mm Hg). The obtained polyol/support was a white powder which was crushed and sieved.

5.5 g of the obtained polyol/support was mixed with 50 mL methanol. To this mixture, 4.5 g polyethylenimine (molecular weight $M_w$ of 25,000) dissolved in 50 mL methanol was added stepwise to ensure good dispersion of polyethylenimine on the polyol/support. The solution was then mixed under brisk stirring for an additional hour. Thereafter, the solvent was removed from the mixture by heating at 50° C. under vacuum on a rotovap followed by overnight vacuum (<1 mm Hg). The resulting supported amine/polyol sorbent was a white powder, which was crushed and sieved to produce a uniform powder.

Example III

Preparation of a Supported Amine/Polyol Sorbent

The same procedure described in Example II was used to prepare a sorbent composed of 47.5 wt. % polyethyleminine (molecular weight $M_w$ of 25,000), 10 wt. % polyethylene glycol (molecular weight $M_w$ of 400), and 42.5 wt. % fumed silica having a primary particle size of 7 nm. The obtained polyol/amine supported sorbent was a white solid, which was ground and sieved to produce a uniform powder. The powder had excellent flow characteristics.

Example IV

Measurement of $CO_2$ Absorption Capacity Using a Static System $CO_2$ absorption data was obtained using an apparatus composed of glass tubes connected to a gas delivery and vacuum system. $CO_2$-containing gases were passed over pre-weighed amounts of absorbents prepared according to the invention. The weight increase of the absorbent was monitored until saturation, i.e., until there was no further weight increase. $CO_2$ absorption was determined by the increase in weight. Desorption of $CO_2$ was achieved by heating the sample at 80 to 110° C. under vacuum (<1 mm Hg) for 1 hr. Desorption capacity was determined by monitoring the weight decrease.

The absorption measurements obtained with some of the absorbents are summarized in Table 1.

TABLE 1

$CO_2$ absorption capacity measurements under static conditions

| Absorbent (ratio by weight) | Absorption temperature (° C.) | $CO_2$ absorption (mg $CO_2$/g absorbent) |
|---|---|---|
| Nano-structured fumed silica supported | | |
| fumed silica/PEI (LMW) (50/50) | 70 | 144 |
|  | 85 | 146 |
| hydrophobic fumed silica/PEI (HMW) (50/50) | 85 | 133 |
| fumed silica/PEI (HMW)/PEG (45/45/10) | 27 | 142 |
| fumed silica/PEI (HMW)/PEG (42.5/47.5/10) | 27 | 148 |
|  | 85 | 181 |
|  | 85 | 197 |
| fumed silica/pentaethylenehexamine (50/50) |  |  |
| fumed silica/tetraethylenepentamine (50/50) |  |  |
| Nano-structured precipitated silica supported | | |
| precipitated silica/PEI (LMW) (50/50) | 70 | 144 |
|  | 85 | 149 |
| precipitated silica/PEI (HMW) (50/50) | 50 | 110 |
|  | 70 | 130 |
| precipitated silica/PEI (linear) (50/50) | 70 | 178 |
| precipitated silica/pentaethylenehexamine (50/50) | 70 | 185 |
| precipitated silica/tetraethylenepentamine (50/50) | 70 | 195 |

PEI (HMW): polyethylenimine of molecular weight Mw ca. 25,000
PEI (LMW): polyethylenimine of molecular weight Mw ca. 800
PEG: polyethylene glycol Mn ca. 400

Example V

Measurement of $CO_2$ Absorption Capacity Using a Thermogravimetric Analyzer $CO_2$ absorption data was obtained using a thermogravimetric analyzer (Shimadzu TCA-50). The powdered absorbent (5-20 mg) was loaded into a platinum crucible and placed on the instrument balance. The solid absorbent was then pretreated at the desired temperature, generally 90 to 110° C. for 1 hr under a flow of nitrogen. Subsequently, the sample was cooled to the desired absorption temperature and the gas flow switched to either $CO_2$ or a mixture of $CO_2$ in different proportions with other gases (e.g., $N_2$, $O_2$, natural gas, etc.). The change in mass in the sample was recorded over time to determine the $CO_2$ absorption capacity. Examples of absorption measurements obtained with this method for the absorbent prepared according to Example III (47.5 wt. % PEI, 10 wt. % PEG and 42.5 wt. % fumed silica) are summarized in Table 2.

TABLE 2

Measurement at 50° C. of $CO_2$ absorption capacity of an absorbent composed of 47.5% PEI, 10% PEG and 42.5% nano-structured fumed silica[1] using a thermogravimetric analyzer

| Gas composition | $CO_2$ absorption (mg $CO_2$/g absorbent) |
|---|---|
| 100% $CO_2$ | 140 |
| 10% $CO_2$ in $N_2$ | 92 |
| 370 ppm $CO_2$ (0.0370%) in air (80% $N_2$, 20% $O_2$) | 27 |

[1]PEI: polyethylenimine of molecular weight Mw ca. 25,000
PEG: polyethylene glycol Mn ca. 400

Example VI

Repeated Absorption-Desorption Cycles

The solid sorbent of Example III was subjected to multiple cycles of absorption and desorption, and absorption-desorption cycles were measured using the static experimental conditions described in Example IV (with 3 minutes for absorption at room temperature with pure carbon dioxide and 10 minutes for desorption at 110° C.). The $CO_2$ absorption capacity of the absorbent remained unchanged after ten absorption-desorption cycles (see Table 3). The data shows that the sorbent according to the invention is capable of a number of repeated absorption-desorption cycles without diminished absorption capacity and can be used well over ten absorption-desorption cycles.

TABLE 3

Repeated $CO_2$ absorption-desorption cycles

| Cycle | 1 | 2 | 3 | 4 | 5 | 6 | 7 | 8 | 9 | 10 |
|---|---|---|---|---|---|---|---|---|---|---|
| Absorption Capacity (mg $CO_2$/g absorbent) | 105 | 106 | 114 | 113 | 112 | 115 | 116 | 118 | 117 | 117 |

What is claimed is:

1. A solid carbon dioxide sorbent for absorbing carbon dioxide from a gas mixture and which is capable of releasing the absorbed carbon dioxide when treated for regeneration, the sorbent comprising an amine in an amount of at least 25% by weight of the sorbent and nano-sized solid particles having a primary particle size that is less than about 100 nm for providing structural integrity and support for the amine and a high surface area for amine-gas contact.

2. The sorbent according to claim 1, wherein the nano-structured support is a nanosilica, silica-alumina and the like fumed or precipitated oxide, calcium silicate, carbon nanotube, or mixture thereof.

3. The sorbent according to claim 1, wherein the amine is a primary, secondary, or tertiary amine or alkanolamine, aromatic amine, or mixtures or combinations thereof.

4. The sorbent according to claim 1, wherein the amine is monoethanolamine (MEA), diethanolamine (DEA), methyldiethanolamine, 2-(2-aminoethylamino)-ethanol, diisopropanolamine, 2-amino-2-methyl-1,3-propanediol, triethanolamine, tetraethylenepentamine, pentaethylenehexamine, or polyethyleneimine.

5. The sorbent according to claim 4, wherein the amine is a linear or branched polyethyleneimine having a molecular weight greater than 600.

6. The sorbent according to claim 1, in which the amine is present in an amount of about 25% to 75% by weight of the sorbent.

7. The sorbent according to claim 1, which further comprises a polyol in an amount up to about 25% by weight of the sorbent.

8. The sorbent according to claim 7, wherein the polyol is selected from the group consisting of glycerol, oligomers of ethylene glycol, polyethylene glycol, polyethylene oxides, and ethers, modifications and mixtures thereof.

9. The sorbent according to claim 1, wherein the nano-sized particles are nanosilica, the amine is polyethyleneimine in an amount of about 25% to 75% by weight of the sorbent, and the sorbent further comprises polyethylene glycol in an amount up to 25% by weight of the sorbent.

10. The sorbent according to claim 1, which releases absorbed carbon dioxide when treated for regeneration.

11. The sorbent according to claim 10, wherein the sorbent is treated with sufficient heat, reduced pressure, vacuum, gas purge, or a combination thereof to release a substantial amount or all the absorbed carbon dioxide.

12. A method for preparing the sorbent of claim 1, which comprises dispersing the nano-sized particles in a solvent to form a suspension;

dissolving the amine in the solvent to form an amine solution; combining the suspension and the amine solution; and removing the solvent to form the sorbent.

13. The method according to claim 12, which further comprises adding a polyol in the amine solution or the suspension before combining the solution and the suspension.

14. The method according to claim 12, which further comprises adding a polyol to the suspension; drying the suspension after the addition of the polyol to form a supported polyol; dispersing the supported polyol in the solvent; and combining the dispersed supported polyol and the amine solution prior to removing the solvent to form the sorbent.

15. A method for continuously capturing and separating carbon dioxide from a gas mixture with a sorbent, which comprises exposing the sorbent according to claim 1 to the gas mixture to effect absorption of carbon dioxide by the sorbent and treating the sorbent that contains absorbed or entrapped carbon dioxide to release a substantial amount or all the absorbed carbon dioxide.

16. The method according to claim 15, wherein the sorbent is provided in a fixed, moving, or fluidized bed and the gas and bed are in contact for a sufficient time to trap the carbon dioxide in the sorbent.

17. The method according to claim 15, wherein the sorbent is treated with sufficient heat, reduced pressure, vacuum, gas purge, or a combination thereof to release the absorbed carbon dioxide.

18. The method according to claim 17, wherein the sorbent is treated when up to 90% of the amine is complexed with carbon dioxide.

19. The method according to claim 15, which further comprises reacting the released carbon dioxide to form useful products.

20. The method according to claim 19, wherein carbon dioxide is used to produce methanol by (a) electrochemical reduction of carbon dioxide in water or (b) reducing carbon dioxide under conditions sufficient to produce an intermediate compound and catalytically hydrogenating the intermediate compound with hydrogen under conditions sufficient to form methanol.

21. The method according to claim 20, wherein the intermediate compound is methyl formate.

22. The method according to claim 19, which further comprises reducing the carbon dioxide under conditions sufficient to carbon monoxide, reacting the carbon monoxide with methanol under conditions sufficient to obtain methyl formate, and catalytically hydrogenating the methyl formate under conditions sufficient to produce methanol.

23. The method according to claim 19, which further comprises dehydrating the methanol under conditions sufficient to produce dimethyl ether.

24. The method according to claim 23, which further comprises heating the dimethyl ether in the presence of an acidic-basic or zeolitic catalyst under conditions sufficient to form ethylene and/or propylene.

25. The method according to claim 24, which further comprises converting the ethylene and/or propylene under conditions sufficient to higher olefins, a synthetic hydrocarbons, aromatics, or a product produced therefrom, for use as a feedstock for chemicals or as transportation fuel.

26. The method according to claim 24, which further comprises hydrating the ethylene or propylene under conditions sufficient to form ethanol or propanol.

* * * * *